United States Patent
Kim et al.

(10) Patent No.: US 9,518,962 B2
(45) Date of Patent: Dec. 13, 2016

(54) GAS CHROMATOGRAPHY CHIP AND MULTI-LAYERED GAS CHROMATOGRAPHY CHIP ASSEMBLY THEREOF

(71) Applicants: Sang-Goo Kim, Seoul (KR); Sung-Min Lim, Seoul (KR)

(72) Inventors: Sang-Goo Kim, Seoul (KR); Sung-Min Lim, Seoul (KR)

(73) Assignee: Korea Basic Science Institute, Yuseong-Gu (KR)

( * ) Notice: Subject to any disclaimer, the term of this patent is extended or adjusted under 35 U.S.C. 154(b) by 352 days.

(21) Appl. No.: 13/717,836

(22) Filed: Dec. 18, 2012

(65) Prior Publication Data

US 2014/0157867 A1    Jun. 12, 2014

(30) Foreign Application Priority Data

Dec. 7, 2012  (KR) .................. 10-2012-0142018

(51) Int. Cl.
*G01N 7/00*    (2006.01)
*G01N 30/30*   (2006.01)
*G01N 30/60*   (2006.01)

(52) U.S. Cl.
CPC .......... *G01N 30/30* (2013.01); *G01N 30/6095* (2013.01)

(58) Field of Classification Search
CPC ............ G01N 30/30; G01N 2030/3084; G01N 2030/025; G01N 2030/3007; G01N 30/54
USPC .............. 73/23.25, 1.43, 23.22, 61.52, 23.35
See application file for complete search history.

(56) References Cited

U.S. PATENT DOCUMENTS

| | | | | |
|---|---|---|---|---|
| 3,581,573 A | * | 6/1971 | Purcell | G01N 30/18 73/23.42 |
| 4,935,040 A | * | 6/1990 | Goedert | G01N 30/20 210/198.3 |
| 5,205,845 A | | 4/1993 | Sacks | |
| 2006/0144237 A1 | * | 7/2006 | Liang | G01N 30/6095 96/101 |

(Continued)

FOREIGN PATENT DOCUMENTS

JP  2003-043022 A   2/2003
KR  19950038382 B1  4/1999

OTHER PUBLICATIONS

Narayanan, S., Alfeeli, B., Agah, M., A Micro Gas Chromatography Chip with an Embedded Non-Cascaded Thermal Conductivity Detector. Proc. Eurosensors XXIV, Sep. 5-8, 2010, Linz, Austria.

*Primary Examiner* — Eric S McCall
*Assistant Examiner* — Mohammed E Keramet-Amircolai
(74) *Attorney, Agent, or Firm* — Chapin Intellectual Property Law, LLC

(57) ABSTRACT

Disclosed is a gas chromatography chip including: a substrate having an upper substrate and a lower substrate; a gas supply connecting part formed on one plane of one surface of the substrate or on one plane of an opposite surface of the substrate; a gas discharge connecting part formed another plane of the one surface of the substrate or on another plane of the opposite surface of the substrate; a micro channel continuously extending from the gas supply connecting part to the gas discharge connecting part to form a micro channel part and having a circular cross-section; at least two position alignment markers formed on one surface or an opposite surface of the opposite surfaces of the substrate; and a heat transfer part and a temperature control unit for controlling a temperature of the substrate.

8 Claims, 7 Drawing Sheets

(56) References Cited

U.S. PATENT DOCUMENTS

2009/0272270 A1* 11/2009 McGill ................ B01J 20/205
  96/101
2013/0125621 A1* 5/2013 Puget .................... G01N 30/60
  73/23.39
2013/0153420 A1* 6/2013 Hu .............................. 204/451

* cited by examiner

FIG. 2

|  | First etching | Second etching | Third etching |
|---|---|---|---|
| Depth(μm) | 18.95 | 33.10 | 56.43 |
|  | 17.63 | 32.83 | 41.51 |
|  | 17.07 | 49.98 | 49.88 |
|  | 19.58 | 40.64 | 49.87 |
| Average | 18.29 | 39.14 | 49.42 |
| Standard deviation | 1.150 | 8.08 | 6.11 |

(a)

(b)

(a)

(b)

GAS CHROMATOGRAPHY CHIP AND MULTI-LAYERED GAS CHROMATOGRAPHY CHIP ASSEMBLY THEREOF

CROSS-REFERENCE TO RELATED APPLICATION

This application claims the benefit under 35 U.S.C. §119 of Korean Patent Application No. 10-2012-0142018, filed on Dec. 7, 2012 in the Korean Intellectual Property Office, the entirety of which disclosure is incorporated herein by reference.

BACKGROUND OF THE INVENTION

1. Field of the Invention

The present invention relates to a gas chromatography chip and a multi-layered gas chromatography chip assembly thereof, and more particularly to a gas chromatography chip produced through multi-etching, and a multi-layered gas chromatography chip assembly obtained by stacking the gas chromatography chips.

2. Description of the Related Art

Chromatography refers to an analysis technology for precisely separating components from a multi-component mixture including not only a simple mixture, but also a very complex mixture.

The chromatography may be variously classified according to types of stationary phases, in particular, types of mobile phases (moving phases).

The chromatography may be classified into a gas chromatography and a liquid chromatography according to types of mobile phases. In the present invention, a description of a liquid chromatography will be omitted.

The gas chromatography technology uses the characteristics in which a trace of a mobile phase is left on a stationary phase according to an attractive force or a suction force of a mixture contained in the mobile phase with respect to the stationary phase if the mobile phase in which the mixture is dispersed is moved through the stationary phase.

That is, according to the gas chromatography technology, the mixture to be separated is contained in the mobile phase. The mixture components are moved through the stationary phase, and the components constituting the mixture are separated while being moved through the stationary phase.

The gas chromatography is especially convenient, prompt, and highly sensitive, and has a high resolution for a thermally stable volatile material.

By using the chromatography, the components of an arbitrary mixture can be precisely separated.

Then, in the case of a gas chromatography chip for analyzing a very complex mixture, a resolution difference is generated by an entire length of a micro channel, that is, a stationary phase, and a polarity formed in the micro channel (stationary phase).

Meanwhile, a gas chromatography chip manufactured according to the related art employs a dry reactive ion etching (DRIE) technique.

Hereinafter, a method of imprinting a desired pattern on a substrate (wafer) will be briefly described.

In order to imprint a desired pattern on a substrate, (1) a substrate suitable for imprinting a pattern is prepared and a thin film is formed on the substrate by using a material suitable for etching, (2) a pattern to be imprinted on the substrate, that is, a design is prepared, and (3) a desired pattern is imprinted by removing an unnecessary portion from the thin film formed on the substrate according to the pattern drawn in the design by using etching equipment.

The imprinting of a pattern may be classified into a dry etching technique and a wet etching technique.

The DRIE technique is a dry etching technique, in which an etching gas that reacts with a substrate (wafer) is converted into a plasma state and the etching gas having the plasma state collides with the substrate to etch a portion of the substrate through the combination of a physical impact and a chemical reaction between the etching gas and components of the substrate.

The dry etching technique uses a complex apparatus, which makes the technique troublesome and causes excessive costs.

Meanwhile, a wet etching technique refers to a technology of allowing chemicals or chemical materials to flow on a surface of a substrate to remove an unnecessary portion from a thin film formed on the surface of the substrate, and can employs a relatively simple and inexpensive apparatus as compared with the dry etching technique.

A technology related to the present invention is disclosed in Korean Patent Registration No. 10-0243995 (issued on Feb. 1, 2000).

SUMMARY OF THE INVENTION

Accordingly, the present invention has been made keeping in mind the above problems occurring in the prior art, and an object of the present invention is to provide a gas chromatography chip employing a transparent substrate and an inexpensive wet etching method.

Since the gas chromatography chip of the present invention employing the transparent substrate cannot obtain a micro channel having a desired depth through single etching, multi-etching is preferably performed.

Further, the substrate is effectively sealed by bonding the substrate in a simple method.

In addition, a polarity of a stationary phase formed in the micro channel on the substrate is adjusted.

Further, in addition to the single gas chromatography chip, the present invention provides a multi-layered gas chromatography chip assembly in which gas chromatography chips obtained through multi-etching are stacked in a multi-layer structure.

The objects of the present invention are not limited to the above-mentioned objects, and other objects will be clearly understood by those skilled in the art.

In accordance with one aspect of the present invention, there is provided a gas chromatography chip including: a substrate having an upper substrate and a lower substrate; a gas supply connecting part formed on one plane of one surface of the substrate or on one plane of an opposite surface of the substrate; a gas discharge connecting part formed another plane of the one surface of the substrate or on another plane of the opposite surface of the substrate; a micro channel continuously extending from the gas supply connecting part to the gas discharge connecting part to form a micro channel part and having a circular cross-section; at least two position alignment markers formed on the one surface or the opposite surface of the substrate; and a heat transfer part and a temperature control unit for controlling a temperature of the substrate, wherein the gas supply connecting part has a tapered shape a width thereof is large at a gas supply hole and becomes narrower toward the micro channel, the micro channel is formed through multi-etching in which etching is performed three times or more and is formed on one side surface of the upper substrate, one side surface of the lower substrate, or side surfaces of the upper substrate and the lower substrate facing each other, the gas supply connecting part and the gas discharge connecting part of the substrate are formed through an EDM scheme or sandblasting, and the temperature control unit performs control of a temperature of the substrate and applies a thermal pressure to the substrate to prevent loss of a gas in the micro channel formed in the substrate.

Preferably, a material of the substrate may be one selected from a glass wafer, a quartz wafer, a polydimethylsiloxane wafer, a silicon wafer, a silicate wafer, a borosilicate wafer, and a fused silica wafer In addition, the gas chromatography chip may further include a stationary phase as a sealing member for sealing a bonding surface of the substrate when an entire surface of the substrate on which the micro channel is formed is coated and the upper substrate and the lower substrate are bonded to each other.

In this case, the stationary phase may be a PDMS, and one selected from silica gel, alumina, charcoal, a molecular body, and a porous polymer may be further coated on the micro channel in addition to the PDMS stationary phase to adjust a polarity of the micro channel.

According to exemplary embodiment of the present invention, there is provided a multi-layered gas chromatography chip assembly including a plurality of gas chromatography chips obtained through the multi-etching, wherein a gas discharge connecting part of a preceding gas chromatography chip and a gas supply connecting part of a succeeding gas chromatography chip are connected to each other to extend a length of the micro channel.

A stationary phase further coated on a stationary phase may be different from each other in each layer of the multi-layered gas chromatography chip assembly.

The details of the other embodiments will be contained in the detailed description and the accompanying drawings.

The advantages and/or features of the present invention and a method of achieving them will be apparent with reference to the embodiments together with the accompanying drawings.

However, the present invention is not limited to the embodiments described below, but may be modified in various forms. The embodiments are provided only to fully disclose the present invention and fully inform those skilled in the art to which the present invention pertains of the scope of the present invention, and is defined only by the claims.

The same reference numerals denote the same elements throughout the specification, and sizes, positions, and coupling relationships of the elements may be exaggerated for clarity.

According to the present invention, the gas chromatography chip is advantageous in terms of economy although the gas chromatography chip uses a transparent substrate.

Further, according to the present invention, the gas chromatography chip, in which the substrate is bonded in a simple method and sealed effectively, can be provided.

Further, according to the gas chromatography chip of the present invention, the polarity of the stationary phase formed in the micro channel on the substrate can be adjusted.

Further, according to the present invention, the multi-layered gas chromatography chip assembly can be provided by stacking the gas chromatography chips in a multi-layer structure.

BRIEF DESCRIPTION OF THE DRAWINGS

FIG. 2 is a table representing an etching depth formed in a substrate through multi-etching according to the exemplary embodiment of the present invention;

DETAILED DESCRIPTION OF THE INVENTION

Hereinafter, exemplary embodiments of the present invention will be described with reference to the accompanying drawings.

First, a gas chromatography chip produced according to an exemplary embodiment of the present invention will be described with reference to FIG. 1.

Figure 1:
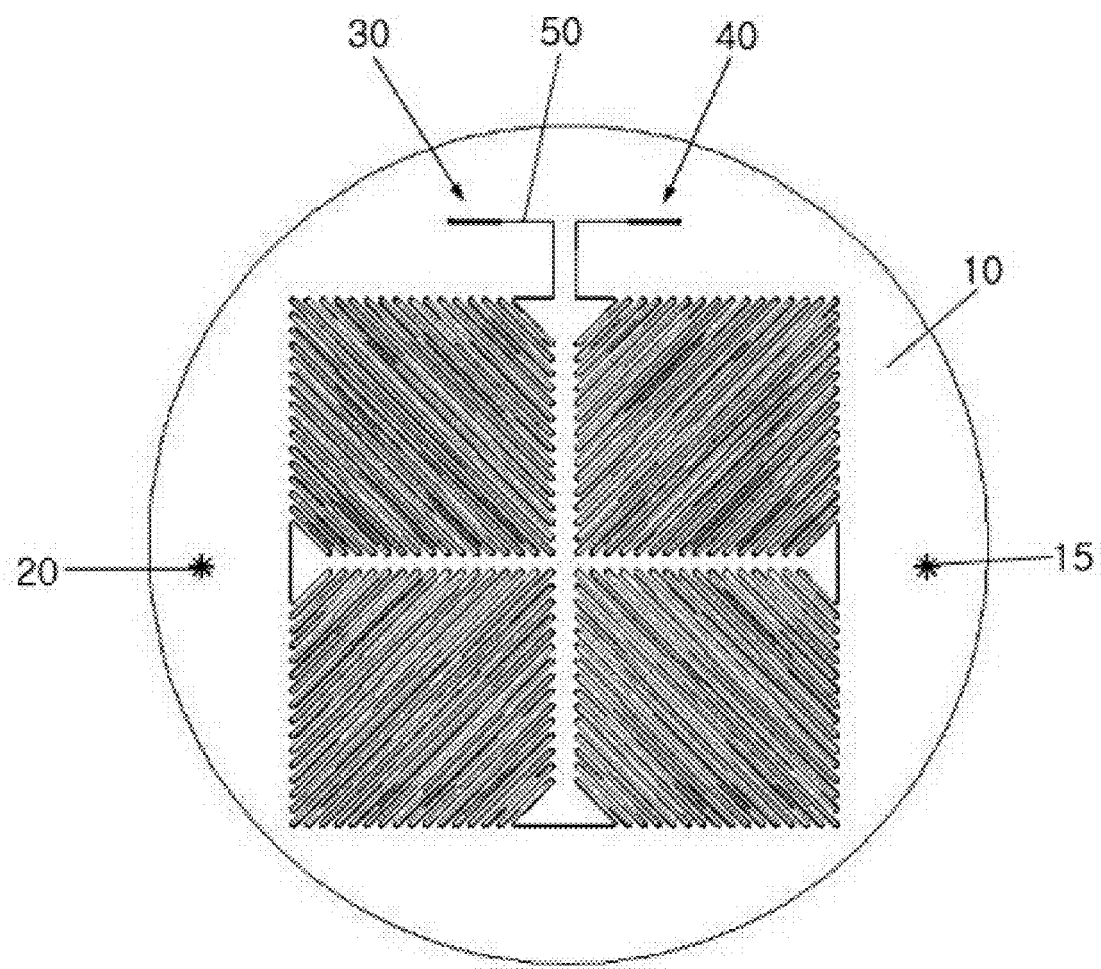
FIG. 1 is a schematic plan view of a gas chromatography chip according to an exemplary embodiment of the present invention.

FIG. 1 is a schematic plan view of a gas chromatography chip according to an exemplary embodiment of the present invention.

Here, the gas chromatography chip includes a circularly formed substrate 10, position alignment markers 15 and 20 formed on one surface of the substrate 10, a gas supply connecting part 30 for supplying a gas to the gas chromatography chip, a gas discharge connecting part 40 for a gas discharged from the gas chromatography chip, a micro channel 50, and a micro channel pattern part 55 in which the micro channel 50 extends to cover almost all flat surface of the substrate 10, starting from one side of the substrate 10.

The substrate 10 may be formed to be separated into an upper substrate and a lower substrate, and the gas supply connecting part 30, the gas discharge connecting part 40, the micro channel 50, and the micro channel pattern part 55 may be formed either of the upper substrate and the lower substrate.

Alternatively, only some of the elements may be formed on any one side of the upper substrate and the lower substrate of the substrate 10, and the remaining elements may be formed on an opposite surface of the upper substrate and the lower substrate of the substrate 10.

Preferably, the material of the substrate 10 is one selected from a glass wafer, a quartz wafer, a polydimethylsiloxane wafer, a silicon wafer, a silicate wafer, a borosilicate wafer, and a fused silica wafer, and most preferably, a borosilicate wafer.

Further, although it is illustrated that the position alignment markers 15 and 20 are formed on both surfaces of the substrate 10 in opposition to each other about the micro channel pattern part 55 on the substrate 10, positions of the position alignment markers 15 and 20 are not limited thereto.

That is, the position alignment markers 15 and 20 may be formed on one surface of the substrate 10 or one surface and an opposite surface of the substrate 10, respectively, and at least two position alignment markers may be provided.

Thus, position alignment markers may be formed adjacent to each other on one surface of the substrate 10, and alternatively, only one position alignment marker may be formed on one surface of the substrate 10, and one surface of the substrate 10 may be cut and then the cut surface may be used as an auxiliary position alignment marker.

In the drawing, the gas supply connecting part 30 may be formed at one side of an upper end of the substrate 10, but may be formed at an arbitrary different position.

The gas supply connecting part 30 is a part used to supply a mixture gas as a mobile phase to the gas chromatography chip produced according to the exemplary embodiment of the present invention.

A gas supply column 60 and a gas supply connector 80 (see FIG. 6) which will be described below are connected to a gas supply side of the gas supply connecting part 30, and a mobile phase gas is supplied through the gas supply column 60 and the gas supply side connector 80.

The gas supplied to the gas supply connecting part 30 flows to a micro channel 50 that is continuously formed.

The micro channel 50 is a micro channel constituting the micro channel pattern part 55, by which a gas having flowed from the gas supply connecting part 30 continuously flows.

The micro channel pattern part 55 is preferably obtained by forming a pattern in advance by using a pattern forming program. After a pattern similar to the one shown in FIG. 1 is formed, the pattern is printed in a blank master (Model name: Photo Plotter Mask, Manufacturer: Barco), and the substrate 10 is etched by using the blank master as a photo mask used in manufacturing of the pattern of the substrate 10 of the present invention.

Then, it will be understood by those skilled in the art to which the present invention pertains that a desired pattern may be formed on the substrate 10 by using a photo mask and a photo resist applied on the substrate 10.

A width of the micro channel pattern part formed according to the exemplary embodiment of the present invention is approximately 100 μm.

Thus, it is apparent that a width of the micro channel 50 formed on the substrate 10 is also substantially the same width.

Meanwhile, a length of the micro channel 50 formed on the substrate 10 may be increased or decreased according to a pattern shape of the micro channel pattern 55.

Further, although the gas discharge connecting part 40 is formed in a direction opposite to an extension direction of the gas supply connecting part 30 formed at one side of an upper end of the substrate 10, the present invention is not limited thereto.

That is, although it is shown in the drawing that the gas supply connecting part 30 and the gas discharge connecting part 40 are formed to have "⌐" and "⌙" shapes, respectively, the gas supply connecting part 30 and the gas discharge connecting part 40 may be formed to face each other as in "⌙" and "⌐" shapes.

Further, the gas supply connecting part 30 and the gas discharge connecting part 40 may be collected at one side of the substrate 10, but may be formed at upper and lower sides or right and left sides of the substrate 10 to be spaced apart from each other.

The gas discharge connecting part 40 is a part for discharging a gas as a mobile phase supplied to the gas chromatography chip produced according to the exemplary embodiment of the present invention.

A gas discharge column 70 and a gas discharge connector 90 (see FIG. 6) are connected to a gas discharge side of the gas discharge connecting part 40, and a gas of a mobile phase is discharged through the gas discharge column 70 and the gas discharge connector 90.

The gas discharged to the gas discharge connecting part 40 may be discharged to the outside, and alternatively, when a multi-layered gas chromatography chip assembly is constituted by layering a gas chromatography chip, the gas may be supplied to the gas supply connecting part (not shown) of another adjacent or remote gas chromatography chip.

That is, a gas discharged from a gas discharge connector installed in a gas discharge connecting part of a preceding gas chromatography chip may be continuously supplied to a gas supply connector installed in a gas supply connecting part of a succeeding gas chromatography chip.

Temperature control of an entire apparatus is very important in the gas chromatography technique, and in particular, there is a need to precisely control temperatures of the substrate 10 and the micro channel 50 formed in the substrate 10 to analyze a mixture at a high resolution.

To this end, although not shown in FIG. 1, a heat transfer part may be further formed at a portion of the substrate 10 other than the position alignment markers 15 and 20, the gas supply connecting part 30, the gas discharge connecting part 40, the micro channel 50, and the micro channel pattern part 55.

Alternatively, the heat transfer part may be formed to heat all of the gas supply connecting part 30, the gas discharge connecting part 40, the micro channel 50, and the micro channel pattern part 55 formed on the substrate 10.

In this case, it is more preferable that a temperature control unit is further installed in the heat transfer part.

In the gas chromatography chip according to the present invention, a temperature of the gas chromatography chip can be controlled rapidly and precisely by the temperature control unit.

Then, the heat transfer part may employ a peltier device by taking the small size of the substrate 10 into consideration.

FIG. 2 is a table representing an etching depth in a substrate through multi-etching according to the exemplary embodiment of the present invention.

As can be seen in FIG. 2, when etching is performed once, a depth of the micro channel 50 is approximately 17 μm to 20 μm (an average depth: 18 μm), but when etching is performed three times, a depth of the micro channel 50 is as large as approximately 42 μm to 57 μm (an average depth: 50 μm).

A depth of the micro channel 50 formed according to the exemplary embodiment of the present invention is 50 μm.

FIGS. 3A and 3B are views showing measurement results of profiles of a micro channel formed on a gas chromatography chip formed according to the exemplary embodiment of the present invention.

Figure 3:
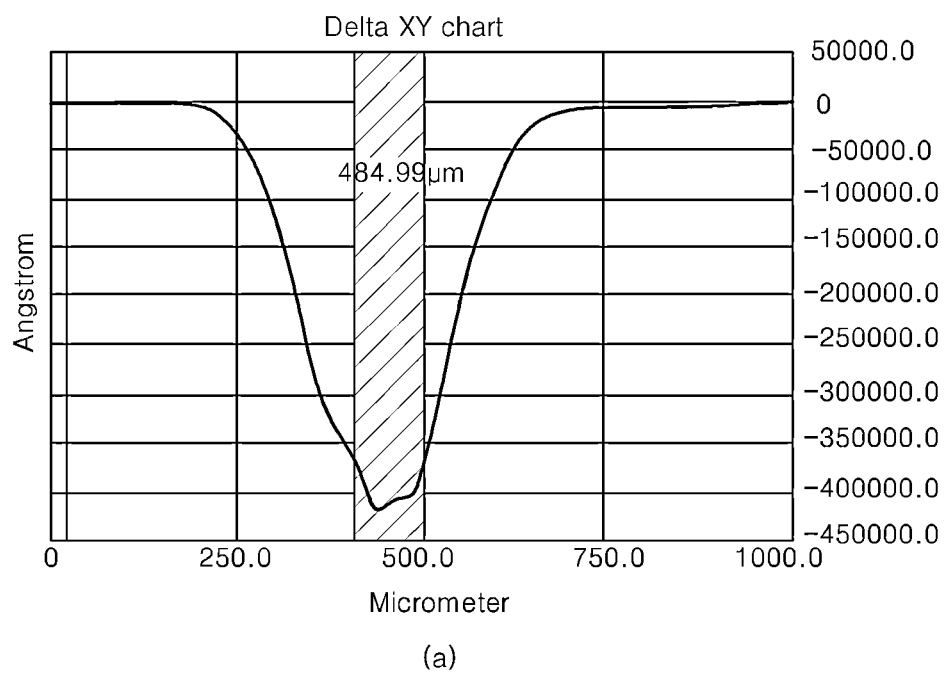
FIGS. 3A and 3B are views showing measurement results of profiles of a micro channel formed on a gas chromatography chip according to the exemplary embodiment of the present invention.
Figure 3:
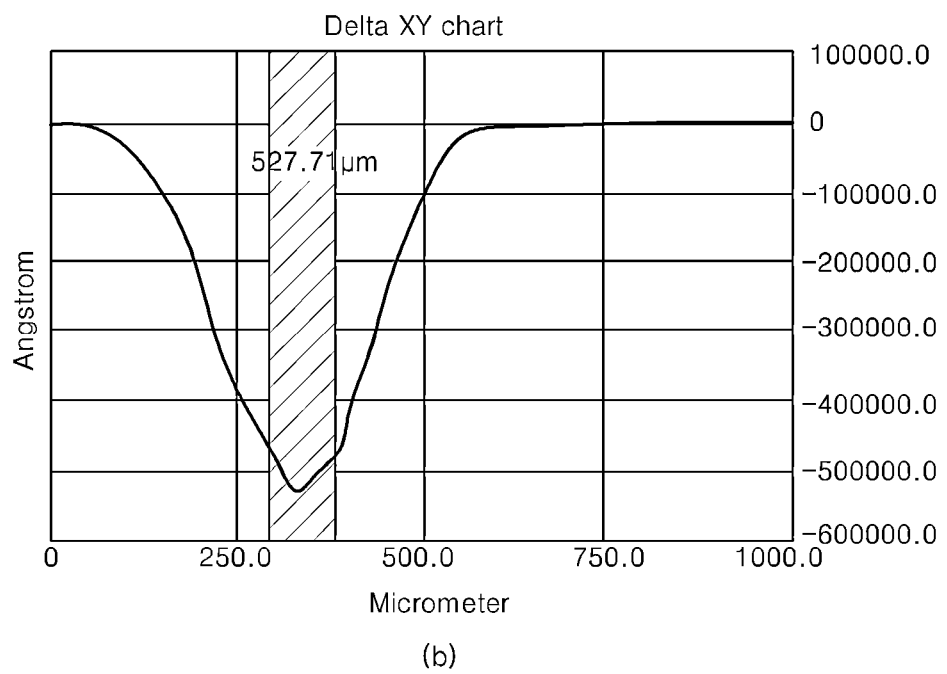

FIG. 3 is a view regarding measurement results of sections by surface profiling to obtain depth data of the micro channel of FIG. 2. As can be seen in FIG. 3, the profiles of the micro channel formed on the gas chromatography chip formed according to the exemplary embodiment of the present invention represent 484.99 μm and 527.71 μm.

Figure 4:
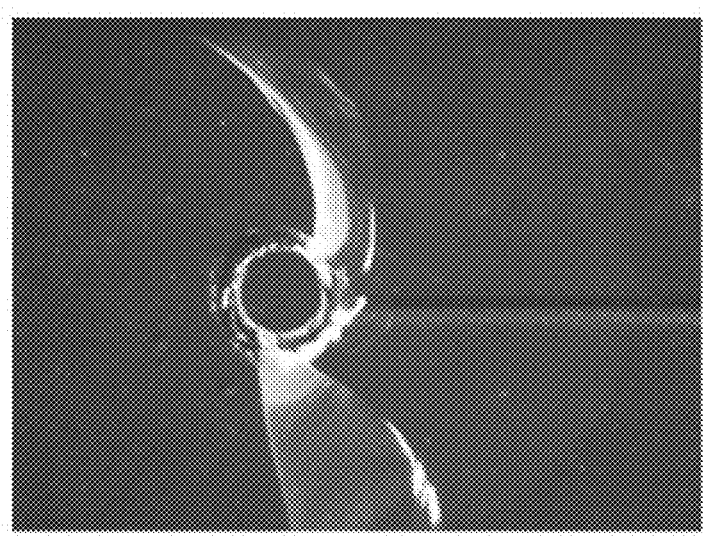
FIG. 4A is a view showing a shape in which a passage width of a gas introduction passage of a gas supply connecting part is the same and FIG. 4B shows a formation pattern of the gas supply connecting part of the gas chromatography chip, in which a passage width of the gas introduction passage of the gas supply connecting part is tapered.
Figure 4:
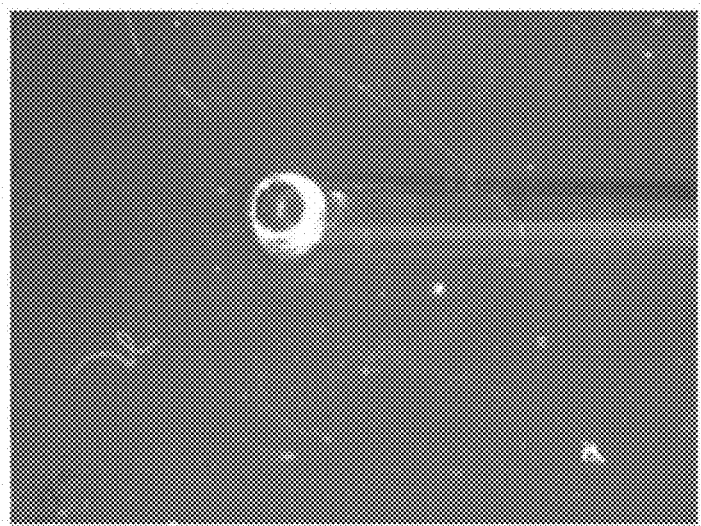

FIG. 4A is a view showing a shape in which a passage width of a gas introduction passage of a gas supply connecting part is the same and FIG. 4B shows a formation pattern of the gas supply connecting part of the gas chromatography chip, in which a passage width of the gas introduction passage of the gas supply connecting part is tapered.

It can be seen that the gas supply passage shown in FIG. 4A itself is formed in parallel, and the gas supply passage shown in FIG. 4B has the largest width at a gas supply hole (a circular portion at the center of the drawing) and becomes narrower as it goes toward the right side.

In the present invention, the reason why the gas introduction passage of the gas supply connecting part has a tapered shape is that when the passage is formed as in FIG. 4A, an amount of the gas having flowed through the micro channel 50 of the substrate 10 and having been discharged to the gas discharge connecting part of the substrate 10 is too small.

In FIG. 4B, the gas introduction passage of the gas supply connecting part is tapered such that the gas supply hole has a width of approximately 500 μm and a width thereof is reduced to approximately 100 μm until the starting point of the micro channel pattern part 55.

A detailed shape thereof will be described with reference to FIG. 5.

Figure 5:
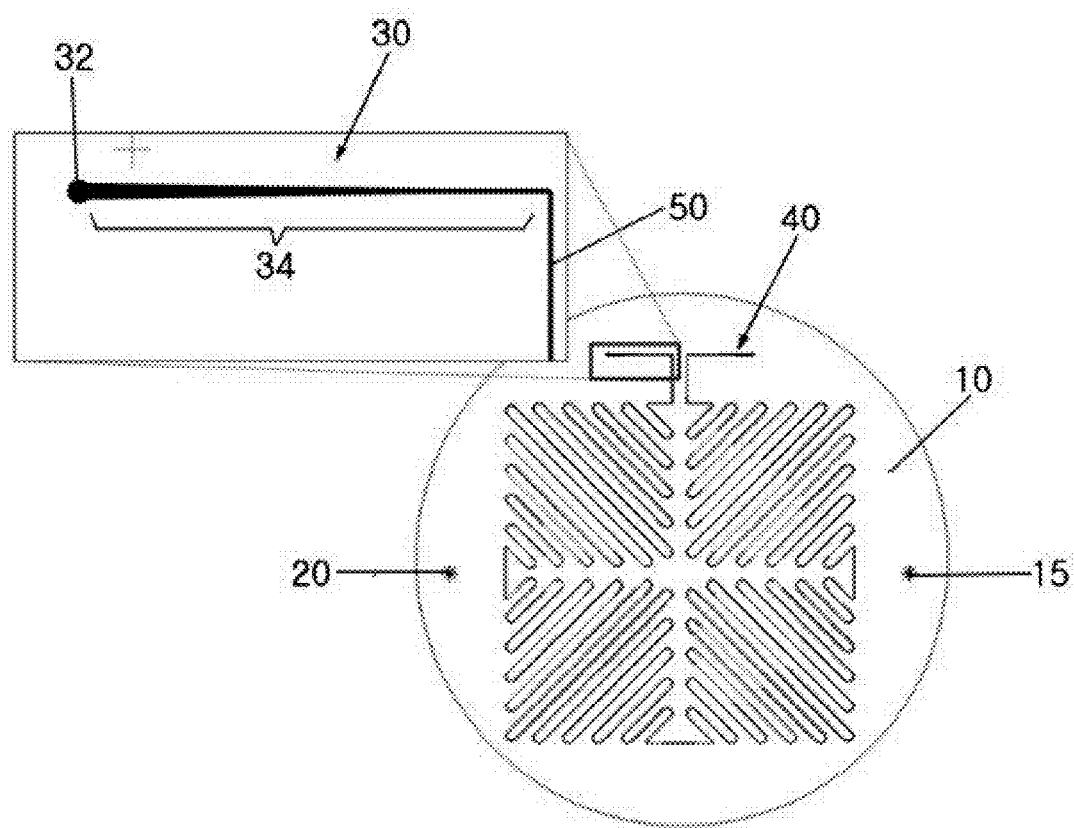
FIG. 5 shows a partially enlarged view of a gas supply connecting part of a gas chromatography chip together with a schematic plan view of the chromatography chip according to the exemplary embodiment of the present invention.

FIG. 5 shows a partially enlarged view of a gas supply connecting part of a gas chromatography chip together with a schematic plan view of the chromatography chip according to the exemplary embodiment of the present invention.

As can be seen in FIG. 5, since a width of a passage around the gas supply hole 32 formed in the gas supply connecting part 30 of the gas chromatography chip according to the exemplary embodiment of the present invention is 500 μm and a width of a passage at a portion far away from the gas supply hole 32 is approximately 100 μm, they form a taper shape channel part 34.

Figure 6:
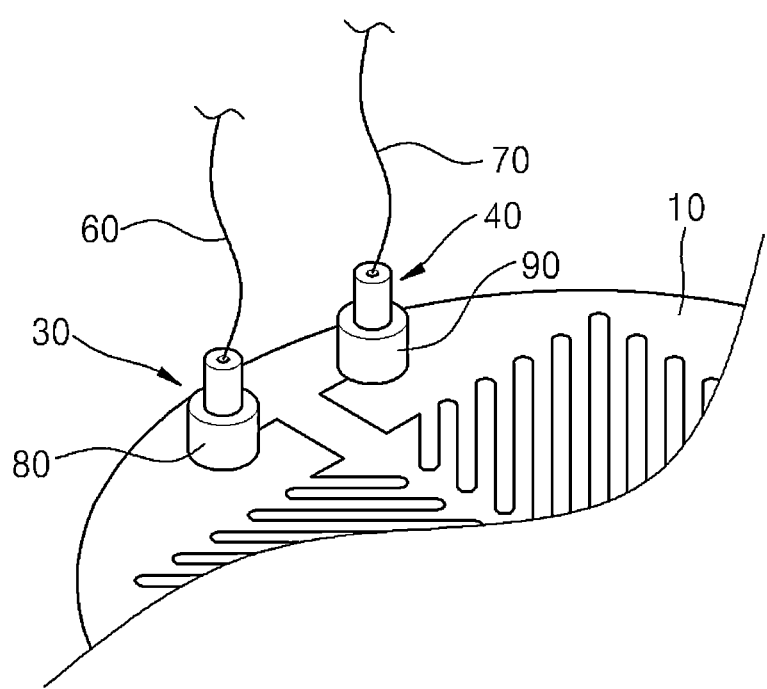
FIG. 6 shows an actual picture of the gas supply connecting part, the micro channel, and the gas discharge connecting part of the gas chromatography chip according to the exemplary embodiment of the present invention, and an appearance of the gas supply/discharge connectors formed in the gas supply connecting part and the gas discharge connecting part.

FIG. 6 shows an actual picture of the gas supply connecting part, the micro channel, and the gas discharge connecting part of the gas chromatography chip according to the exemplary embodiment of the present invention, and an appearance of the gas supply/discharge connectors formed in the gas supply connecting part and the gas discharge connecting part.

As can be seen in FIG. 6, in the gas chromatography chip according to the exemplary embodiment of the present invention, the gas supply connector 80 is installed in the gas supply hole 32 of the gas supply connecting part 30 formed at one side of the substrate 10, and the gas discharge connector 90 is installed in the gas discharge hole (not shown) of the gas discharge connecting part 40 formed at an opposite side of the substrate 10.

According to the exemplary embodiment of the present invention, Nanoport Assembly (R) (manufacturer: UpChurch Scientific (U.S.A.)) is used as the gas supply connector 80 and the gas discharge connector 90. Since Nanoport Assembly (R) is a polyether ether ketone (PEEK) material, it satisfies a condition of a desired thermal resistance and a gas is not leaked from an interior of the substrate 10 even when a high pressure is applied to the gas chromatography chip.

Figure 7:
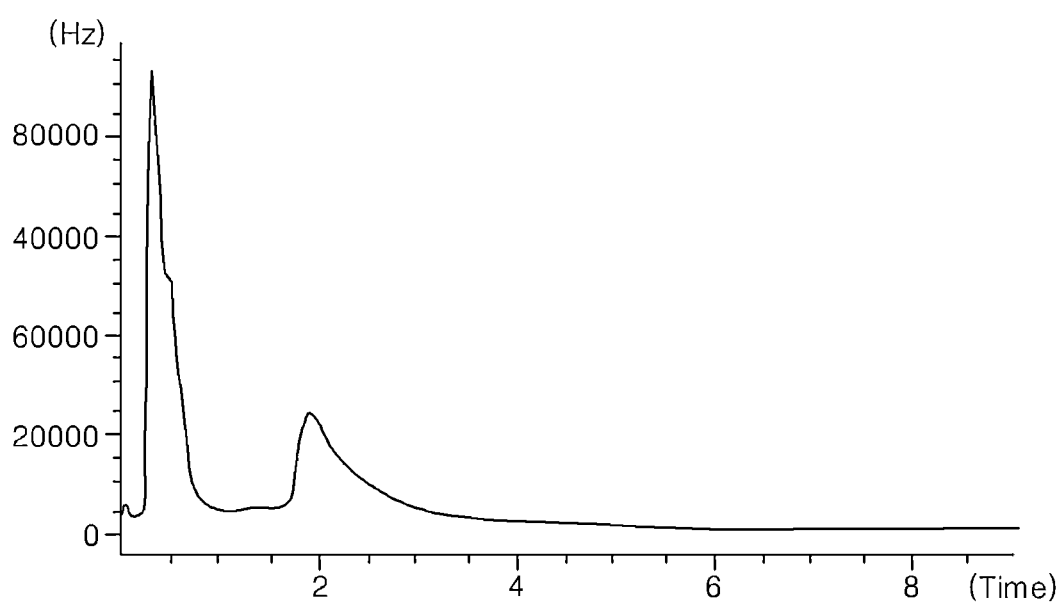
FIG. 7 is a view showing an actual gas analysis result of the gas chromatography chip according to the exemplary embodiment of the present invention, which represents an ECD detection result of chloroform and 4-bromofluorobenzene.

Finally, FIG. 7 is a view showing an actual gas analysis result of the gas chromatography chip according to the exemplary embodiment of the present invention, which represents an ECD detection result of chloroform and 4-bromofluorobenzene.

In order to obtain a graph of FIG. 7, 9 μl of chloroform and 1 μl of 4-bromofluorobenzene are mixed as analysis samples, and hexane is added to be diluted at a ratio of 1/200.

A μECD detector (model name: HP 6890, manufacturer: Agilent of U.S.A.) was used as analysis equipment.

Other analysis conditions are as follows.
Gas supply temperature: 300° C.
Carrier gas: He
Pressure: 1.30 Mpa
Split ratio: 50:1
Amount of supplied gas: 1 μl
Used column: Micro fab column (2 m×0.10 mm ID×0.1 μm)
Temperature ramp: 40° C. (2 min)→10° C./min→120° C. (10 min)
Temperature of detector: 300° C.

As can be seen in FIG. 7, it is clearly represented that the first peak of the graph is chloroform and it is clearly represented that the second peak of the graph is 4-bromofluorobenzene.

Next, a method of implementing the gas chromatography chip and the multi-layered chromatography chip assembly according to the exemplary embodiment of the present invention will be described. Since some items have been described already, description about redundant parts may be omitted.

First, a substrate including an upper substrate and a lower substrate is prepared.

Preferably, the material of the substrate is one selected from a glass wafer, a quartz wafer, a polydimethylsiloxane wafer, a silicon wafer, a silicate wafer, a borosilicate wafer, and a fused silica wafer, and most preferably, a borosilicate wafer.

Further, as described above, a micro channel having a width of approximately 100 μm is formed by applying a photo resist (PR) and a wet etching method to the borosilicate wafer by using a mask having a desired pattern.

A width of the micro channel in the mask is 0.1 mm, a diameter of a gas supply connecting part and a gas discharge connecting part is 0.5 mm, and an entire length of the micro channel is 6054 mm.

Then, the wet etching is preferably repeated three times or more until a desired etching depth, that is, 50 μm is obtained.

The micro channel 50 or the micro channel pattern part 55 may be formed one surface of any one of the upper substrate and the lower substrate forming the substrate 10, or facing opposite surfaces of the upper substrate and the lower substrate.

Further, as described above, since etching is repeated by referring to position alignment markers 15 and 20 formed in the substrate 10, the micro channel 50 and the micro channel pattern part 55 having a desired pattern may be etched to accurately have a predetermined depth and a predetermined width, or to be engaged with each other.

In addition, in the borosilicate wafer (4 inches standard) used in the exemplary embodiment of the present invention, Au/Cr is deposited in advance before the micro channel 50 or the micro channel pattern part 55 is imprinted.

Since the deposition film is endurable against hydrofluoric acid, it can be wet-etched more efficiently as compared with a photoresist according to the related art.

Then, an E-beam evaporator (model name: ei-5, manufacturer: ULVAC) is used as the deposition equipment, a thickness of the previously deposited Cr is approximately 200 to 300 Å and a thickness of Au deposited thereon is approximately 2000 Å.

Further, a surface of the substrate on which the Cr and the Au are deposited is a photoresist, and may be coated by SU-8 50 (Microchem of U.S.A.).

The SU-8 50 is a negative etching photo resist, and a coating thickness may be adjusted to 40 to 100 μm during the application.

Thereafter, as described above, etching is performed three times or more, and the obtained cross-section of the micro channel 50 may be preferably circular.

By using the technique, as described above, since a masking layer or other special equipment which are essential in a DRIE technique according to the related art are not necessary, the micro channel pattern part 55 may be formed on the substrate 10 cheaply in a simple method.

Next, polydimethylsiloxane (PDMS) is applied as a stationary phase and for the purpose of bonding/sealing the upper substrate and the lower substrate.

The PDMS is a material having optically transparent, non-polar and nonflammable property and is coated in a spin coating method by using a spin coater.

For reference, the silicate wafer used in the exemplary embodiment of the present invention is also optically transparent.

A rotating speed of the spin coater during spin coating is approximately 4000 to 8000 RPM and a rotation duration time is approximately 1 second.

Further, in order to lower a viscosity of PDMS, the PDMS was diluted by toluene at a ratio of 1:1 or 1:2 (v/v), and thus, a coating height of the PDMS is also restrained as possible.

According to the exemplary embodiment of the present invention, only a surface of any one of the upper substrate and the lower substrate forming the substrate 10 is spin-coated, both of the upper substrate and the lower substrate is bonded to each other while an opposite surface thereof is not applied, and both the substrates are heated in an oven at a temperature of 70° C. for approximately 1 hour to be completely bonded to each other.

Then, the PDMS is preferably coated on a side surface of any one of the upper substrate and the lower substrate constituting the substrate. Alternatively, the PDMS may be coated on both surfaces of the upper substrate and the lower substrate.

Since the coated PDMS may perform a function of the stationary phase and may be directly used to bond the silicate wafer, it can contribute to fluidity of a gas in the micro channel 50 and sealing of the substrate 10.

That is, the PDMS may be manufactured through simple coating using a spin coater, not by a method in which after the gas chromatography is formed, the PDMS is injected into any one of the gas supply connecting part 30 or the gas discharge connecting part 40 to coat a wall surface of the micro channel 50, which is technically difficult.

If necessary, a stationary phase having the other polarity may be additionally applied to a coating layer of the substrate 10.

An example of a stationary phase having the other polarity may include, for example, silica gel, alumina, charcoal, a molecular body, and a porous polymer, and when they are applied as a stationary phase, the polarity of the micro channel 50 can be easily adjusted.

Further, the stationary phase having a different polarity may be applied to any one of the upper substrate and the lower substrate of the substrate 10, and may be applied to the entire micro channel 50.

Moreover, when the multi-layered gas chromatography chip assembly is formed, the same stationary phase may be applied to the gas chromatography chips or different stationary phases may be applied to the gas chromatography chips.

As described above, according to the exemplary embodiment of the present invention, since the chip is manufactured not by a dry etching (DRIE) technique according to the related art but by a wet etching technique, a spin coater having an inexpensive and simple structure can be used so that the process becomes very simple.

According to the exemplary embodiment of the present invention, a specification of the substrate 10 used in the gas chromatography chip is as follows.

Size of substrate: 4 inches
Size of gas supply hole: 50 μm
Size of gas discharge hole: 500 μm
Width of micro channel: 100 μm
Material of substrate: borosilicate wafer It should be noted that a size of the gas supply hole is 500 μm and a width of the micro channel is 100 μm, and thus a passage from the gas supply hole to the micro channel has a tapered shape.

Next, a method of forming the gas supply hole 32 formed in the gas supply connecting part 30 and the gas discharge hole (not shown) formed in the gas discharge connecting part 40 according to the exemplary embodiment of the present invention will be described.

First, it should be noted that the gas supply hole and the gas discharge hole may be accurately formed through sand blasting.

However, since sand blasting is very inefficient for small-scale production, according to the exemplary embodiment of the present invention, the gas supply hole and the gas discharge hole are formed by using electrical discharge machining (EDM).

Then, 5 M of a KOH solution is prepared, the gas chromatography chip of the present invention is completely submerged (at 8 mm or deeper) in the KOH solution, and a current of 40 V/3 A is applied.

If necessary, the EDM electrode and the solution are properly replaced.

The gas supply hole and the gas discharge hole may be simultaneously formed on one side surface of the gas chromatography chip, or one may be formed on one side surface thereof and the other may be formed on an opposite side surface thereof.

The former case is convenient for work, and the latter case is very advantageous when the multi-layered chromatography chip assembly is formed.

Next, a column for supplying a gas mixture which is to be analyzed is connected to the gas chromatography chip obtained according to the exemplary embodiment of the present invention.

To this end, as shown in FIG. 6, the gas supply connector 80 is installed in the gas supply hole 32 of the gas supply connecting part 30 formed at one side of the gas chromatography chip according to the exemplary embodiment of the present invention, and the gas discharge connector 90 is installed in the gas discharge hole (not shown) of the gas discharge connecting part 40 formed at an opposite side of the chip.

The gas supply column 60 in charge of supply of a gas from the outside and the gas discharge column 70 may be connected to the gas supply connector 80 and the gas discharge connector 90.

The gas supply column 60 is a column for supplying the gas of a mobile phase and the gas containing the mixture which is to be analyzed, and the gas discharge column 70 is a column for discharging the gas to the outside or connected to the gas supply connecting part of another gas chromatography chip in the case of the multi-layered gas chromatography chip assembly.

Since the coating of the PDMS, the bonding of the substrate, and the deposition of Au/Cr have been described above, a description thereof will be omitted.

Further, an analysis performance of the gas chromatography chip manufactured according to the exemplary embodiment of the present invention has been also described with reference to FIG. 7.

Here, in order to measure an analysis performance of the gas chromatography chip obtained according to the present invention, the present invention may further include detection apparatuses connected to the gas chromatography chip, for example, a flame ionization detector (FID), an electron capture detector (ECD), and a mass analyzer.

The ECD is mainly useful for detection of a compound containing halogen elements (for example, F, Cl, Br, and I), and mainly used for detection of agricultural chemicals, a PCB, and a $N_2O$ gas. The FID is mainly used to analyze an organic compound, such as HC, TCE, and PCE.

Finally, a heat transfer part may be further formed in the gas chromatography chip obtained according to the exemplary embodiment of the present invention to control the temperature.

The heat transfer part may be formed in an area where accessories of the gas chromatography chip is not formed, and alternatively, may be formed to heat an entire gas chromatography chip.

Further, as described above, the temperature control unit may be preferably further installed in the heat transfer part.

Thus, in the case of the gas chromatography chip according to the present invention, since the temperature of the gas chromatography chip can be controlled rapidly or precisely by the temperature control unit, the temperature can be controlled immediately and effectively as compared with the gas chromatography technique according to the related art, and thus, a very clear peak can be obtained when the gas mixture is analyzed.

The heat transfer part may employ a peltier device by taking the small-size of the gas chromatography chip into consideration.

Further, the heat transfer part controls the temperature of the gas chromatography chip and applies a thermal pressure to the bonding portion of the gas chromatography chip to prevent loss of the gas in the micro channel.

This is because the heat applied to the gas chromatography chip can reinforce a bonding force of the PDMS applied between the upper substrate and the lower substrate.

The detailed embodiments of the present invention have been described until now, but the present invention can be variously modified without departing from the scope of the present invention.

Accordingly, the scope of the present invention should not be limited to the embodiments, but should be determined according to both the claims and their equivalents.

Although the present invention has been described with reference to the embodiments and the drawings, the present invention is not limited to the embodiments, but those skilled in the art to which the present invention pertains can make various modifications and changes from the description.

Therefore, the spirit of the present invention should be recognized by the claims, and their equivalent modifications fall in the scope of the present invention.

What is claimed is:

1. A gas chromatography chip comprising:
   a substrate comprising an upper substrate and a lower substrate;
   a gas supply connecting part formed on one plane of one surface of the substrate or on one plane of an opposite surface of the substrate;
   a gas discharge connecting part formed another plane of the one surface of the substrate or on another plane of the opposite surface of the substrate;
   a micro channel continuously extending from the gas supply connecting part to the gas discharge connecting part to form a micro channel part and having a circular cross-section;
   at least two position alignment markers formed on the one surface or the opposite surface of the substrate;
   a heat transfer part and a temperature control unit for controlling a temperature of the substrate;
   a stationary phase as a sealing member for sealing a bonding surface of the substrate when an entire surface of the substrate on which the micro channel is formed is coated and the upper substrate and the lower substrate are bonded to each other;
   wherein the gas supply connecting part has a tapered shape a width thereof is large at a gas supply hole and becomes narrower toward the micro channel,
   the micro channel is formed through multi-etching in which etching is performed three times or more and is formed on one side surface of the upper substrate, one side surface of the lower substrate, or side surfaces of the upper substrate and the lower substrate facing each other,
   the gas supply connecting part and the gas discharge connecting part of the substrate are formed through an EDM (electrical discharge machining) scheme or sandblasting, and
   the temperature control unit performs control of a temperature of the substrate and applies a thermal pressure to the substrate to prevent loss of a gas in the micro channel formed in the substrate, and
   the stationary phase is a PDMS, and
   wherein the PDMS is applied as the stationary phase and for the purpose of bonding and sealing the upper substrate and the lower substrate.

2. The gas chromatography chip of claim 1, wherein a material of the substrate is one selected from a glass wafer, a quartz wafer, a polydimethylsiloxane wafer, a silicon wafer, a silicate wafer, a borosilicate wafer, and a fused silica wafer.

3. The gas chromatography chip of claim 1, wherein one selected from silica gel, alumina, charcoal, a molecular body, and a porous polymer is further coated on the micro channel in addition to the PDMS stationary phase to adjust a polarity of the micro channel.

4. The multi-layered gas chromatography chip assembly comprising a plurality of gas chromatography chips of claim 1, wherein a gas discharge connecting part of a preceding gas chromatography chip and a gas supply connecting part of a succeeding gas chromatography chip are connected to each other to extend a length of the micro channel.

5. The multi-layered gas chromatography chip assembly comprising a plurality of gas chromatography chips of claim 2, wherein a gas discharge connecting part of a preceding gas chromatography chip and a gas supply connecting part of a succeeding gas chromatography chip are connected to each other to extend a length of the micro channel.

6. The multi-layered gas chromatography chip assembly comprising a plurality of gas chromatography chips of claim 3, wherein a gas discharge connecting part of a preceding gas chromatography chip and a gas supply connecting part of a succeeding gas chromatography chip are connected to each other to extend a length of the micro channel.

7. The multi-layered gas chromatography chip assembly of claim 4, wherein a stationary phase further coated on a stationary phase is different from each other in each layer of the multi-layered gas chromatography chip assembly.

8. The gas chromatography chip of claim 1, wherein said microchannel is formed on one side surface of the upper substrate, one side surface of the lower substrate, or both side surfaces of the upper substrate and the lower substrate facing each other, and where the microchannel also is formed through a multi-etching process in which the microchannel formed by etching of one of the side surfaces of the upper or lower substrate or the side surfaces of both the upper and lower substrates, where the etching comprises performing wet etching three times or more of the respective side surface.

* * * * *